United States Patent
Huynen et al.

(10) Patent No.: US 6,749,808 B1
(45) Date of Patent: Jun. 15, 2004

(54) STERILIZABLE CONTAINER WITH A STERILIZABLE ADAPTER FOR DOCKING TO A PORT OF AN ISOLATION SYSTEM

(75) Inventors: Marc Huynen, Zétrud-Lumay (BE); Stéphane Huynen, Bierbeek (BE); Steven Vanhamel, Herk-de-Stad (BE)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/430,918

(22) Filed: Nov. 1, 1999

(30) Foreign Application Priority Data

Nov. 1, 1998 (EP) .............................................. 98203667

(51) Int. Cl.[7] .............................. A61L 2/08; A61L 2/00; B65D 33/00; B65B 55/02
(52) U.S. Cl. ............................ 422/28; 422/26; 422/32; 422/294; 422/302; 383/33; 383/41; 383/93; 53/425; 53/434
(58) Field of Search ............................ 422/294.1, 302, 422/26, 292, 28, 32–33; 383/33, 93, 37, 41, 80; 53/434, 426, 425

(56) References Cited

U.S. PATENT DOCUMENTS

| | | | |
|---|---|---|---|
| 4,185,754 A | * | 1/1980 | Julius .......................... 221/63 |
| 4,805,378 A | * | 2/1989 | Anderson ..................... 53/426 |
| 4,991,633 A | * | 2/1991 | Wong ............................. 141/5 |
| 5,447,699 A | * | 9/1995 | Papciak et al. ............. 422/294 |
| 5,735,609 A | * | 4/1998 | Norton ......................... 383/33 |

* cited by examiner

Primary Examiner—Robert J. Warden, Sr.
Assistant Examiner—Monzer R. Chorbaji
(74) Attorney, Agent, or Firm—Oliver A. Zitzmann; Steven J. Hultquist

(57) ABSTRACT

A sterilizable container (20) is described which includes a flexible bag (23), the flexible bag (23) having a hole in a flat portion thereof and a hollow connector port (22) fixed thereto, the connector port (22) including a collar portion (22A) and a flange portion (24) defining an internal bore (26) of the connector port (22), the inside surface of the flexible bag (23) being sealed to an outside surface of the flange portion (24) and the collar portion (22A) extending through the hole in the flexible bag (23).

Also disclosed is an adapter (10) having an internal bore (12), the connector port (22) and the adapter (10) being sealably connectable by a clamping and sealing device (11, 13) so that the internal bores (12, 16) of the connector port (22) and the adapter (10) are in open communication. Preferably, the adapter (10) has a removable door (16) sealed to the end of the adapter (10) remote from the sealable connection to the connector port (22).

20 Claims, 13 Drawing Sheets

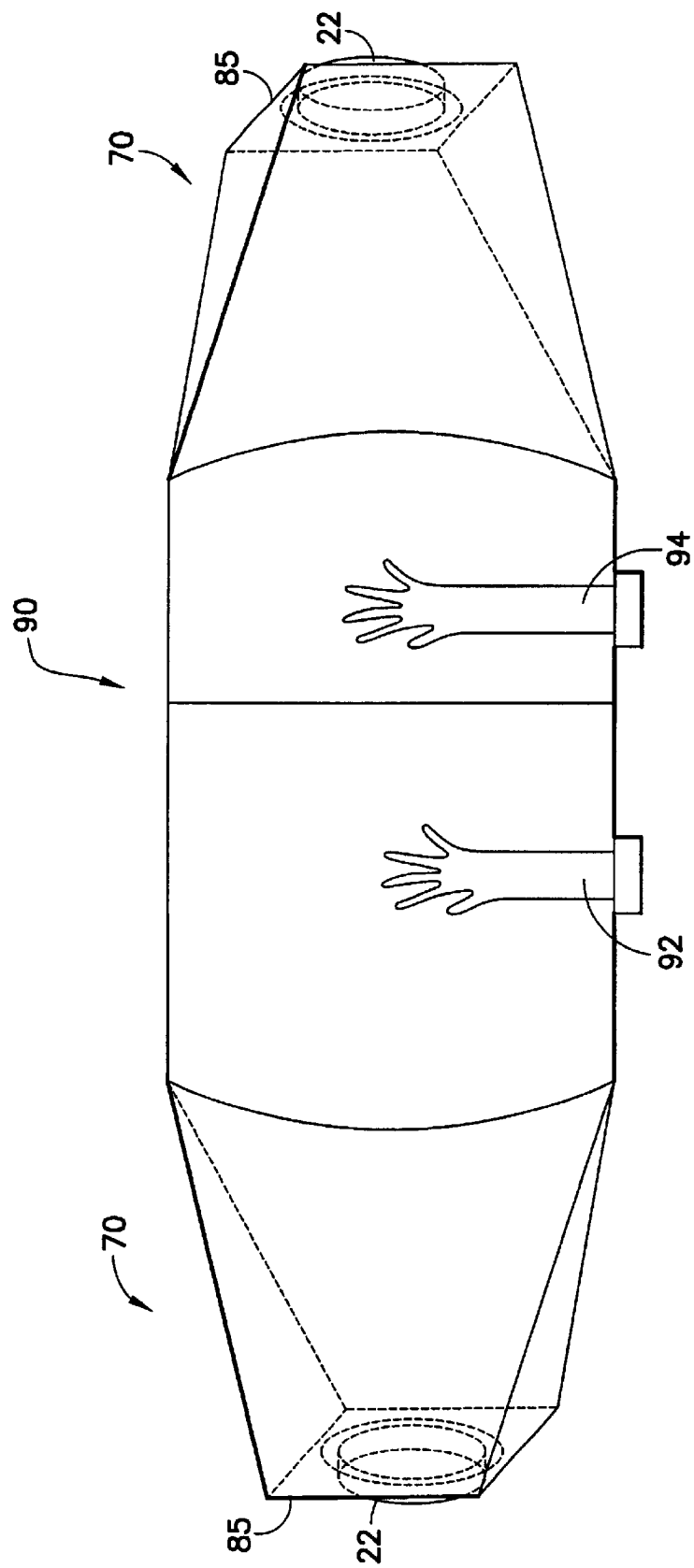

STERILIZABLE CONTAINER WITH A STERILIZABLE ADAPTER FOR DOCKING TO A PORT OF AN ISOLATION SYSTEM

The present invention relates to a sterilisable dockable bag or container which has a sterilisable connector port and a method for attaching to a standard port of a sterile enclosure or isolation system. The ports when combined may be used to transfer sterilized items from the inside of the container to the sterile enclosure or isolation system. The present invention also relates to container combination which may be docked to a standard port of a sterile enclosure or isolation system.

TECHNICAL BACKGROUND

U.S. Pat. No. 5,447,699 (Papciak) describes a combination container for holding sterilized elements and a sterilisable port. The container includes a flexible bag with a hole in it through which a collar with a flange is placed. The collar of the flange is heat sealed to the bag. The collar is sealed with a steam breathable tearable flap on its inside thus leaving a portion of the collar which is contaminated. To decontaminate this collar the port of the isolation system has piping for transferring a treatment fluid to the zone between the tearable flap and the outside of the port of the isolation system. This known bag and port suffers from the disadvantage that a sterilizing step is required after closure of the bag to the port of the isolation system.

U.S. Pat. No. 5,735,609 (Norton) describes a container for holding sterilized elements. In '609 it is argued that the seal of the collar to the bag of '699 is unsatisfactory. Instead, the container of '609 includes a flexible bag having an opening which is attached to a connector port which is engageable with an isolation system. The open end of the bag is slid over the port and is clamped around the port. The open end of the bag is located in a sealing material which is fixed in a groove of the port. The sealing material may be a two-part epoxy. The front opening of the port is sealed by a door. The outer surface of this door is contaminated. The sealing arrangement of '609 is an improvement over a simple design in which the open end of a flexible bag is simply clamped to a cylinder, but the sealing material requires careful location and its curing adds an extra complication to the manufacture of the container.

It is an object of the present invention to provide a sterilisable container combination with a connector port which allows easy manufacture of the container and to provide a relatively simple method for docking the connector port to the port of an isolation system.

It is a further object of the present invention to provide a sterilisable container combination and method of connecting it to an inlet port of an isolation system which avoids complex sealing arrangements or ones which may nave or develop inherent leaks.

It is still a farther object of the present invention to provide a sterilisable container combination and a method of connecting it to an inlet port of an isolation system which does not require an additional sterilization treatment when the container combination is docked to the port of an isolation system.

SUMMARY OF THE INVENTION

The present invention includes a sterilisable container combination comprising: a container having an opening; a hollow connector port having an internal bore, the container being sealingly secured to the connector port so that the opening in the container is in registry with the bore of the connector port; an adapter having an internal bore, the connector port and the adapter being sealably connectable by a damping and sealing device so that the internal bores of the connector port and the adapter are in open communication. Preferably the adapter has a removable door sealed to the end of the adapter remote from the sealable connection to the connector port.

The present invention also includes a plurality of sterilisable containers each having an opening and a hollow connector port having an internal bore, each container being sealingly secured to the connector port so that the opening in the container is in registry with the bore of the connector port; and a plurality of different adapters suitable for connecting to the inlet ports of different isolation systems, each adapter having an internal bore, the connector ports and the adapters being sealingly connectable by a common size of connecting and sealing devices so that the internal bores of the connector port and the adapter are in open communication.

The present invention provides a method of connecting a sterilized container to the inlet port of an isolation system, comprising the steps of: providing a container with a hollow connector port securely sealed to the container; sealingly connecting a first end of an adapter to the connector port of the container; and docking and sealing a second end of the adapter to the inlet port of the isolation system.

The present invention also includes a sterilisable container including a flexible bag, the flexible bag having a hole in a flat portion thereof and a hollow connector port fixed thereto, the connector port including a collar portion and a flange portion defining an internal bore of the connector port the inside surface of the flexible bag being sealed to an outside surface of the flange portion and the collar portion extending through the hole in the flexible bag.

The present invention also includes a method of producing a sterilisable container, comprising the steps of: providing a flexible sheet enclosure with a flat portion; providing a hole in the flat portion of the flexible sheet enclosure and fixing a hollow connector port thereto, the connector port including a collar portion and a flange portion defining an internal bore of the connector port, and sealing the inside surface of the flexible sheet enclosure to an outside surface of the flange portion, the collar portion extending through the hole in the flexible sheet enclosure. The enclosure may extend in one direction to form the container and the sheet material forms the walls of the container the flat portion being provided by a front face of the sheet enclosure perpendicular to the extension direction of the container and the hole is provided in the front face.

The present invention also includes a sterilisable container device comprising a first outer container and an inner flexible container, the outer container including a hollow connector port the connector port being sealed by a removable cover; and the removable cover including a holding device for the inner flexible container on the side of the cover facing towards the inner flexible container.

The dependent claims define further individual embodiments of the present invention. The present invention, its advantages and embodiments will now be described with reference to the following drawings.

BRIEF DESCRIPTION OF THE DRAWINGS

FIG. 14 is an isolation room in accordance with another embodiment of the present invention constructed from two flexible containers as shown in FIG. 13

DESCRIPTION OF THE ILLUSTRATIVE EMBODIMENTS

The present invention will be described with reference to certain embodiments and to certain drawings but the invention is not limited thereto but only by the claims.

Figure 1:
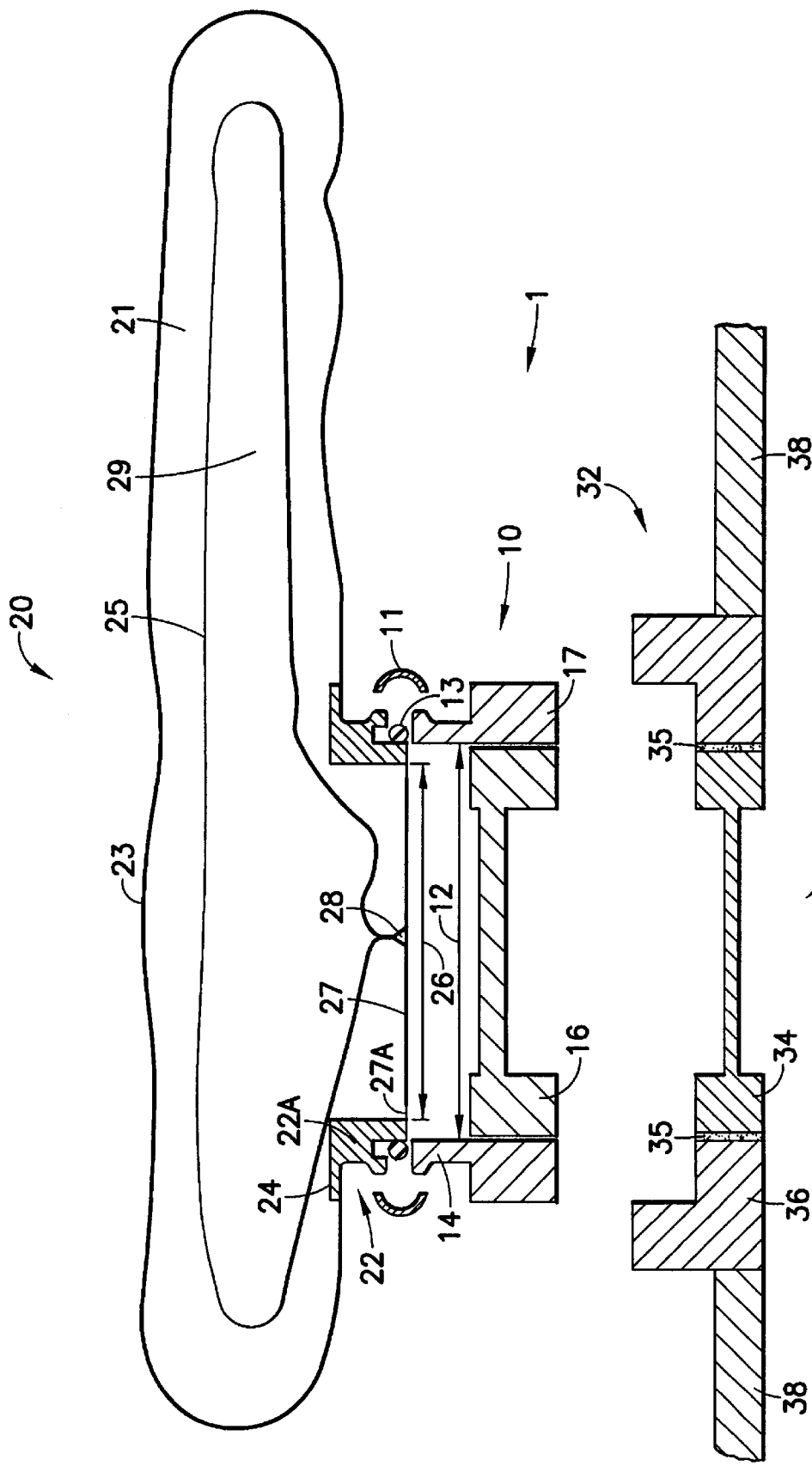
FIG. 1 is a cross-sectional schematic representation of a container combination in accordance with a first embodiment of the present invention.
Figure 2:
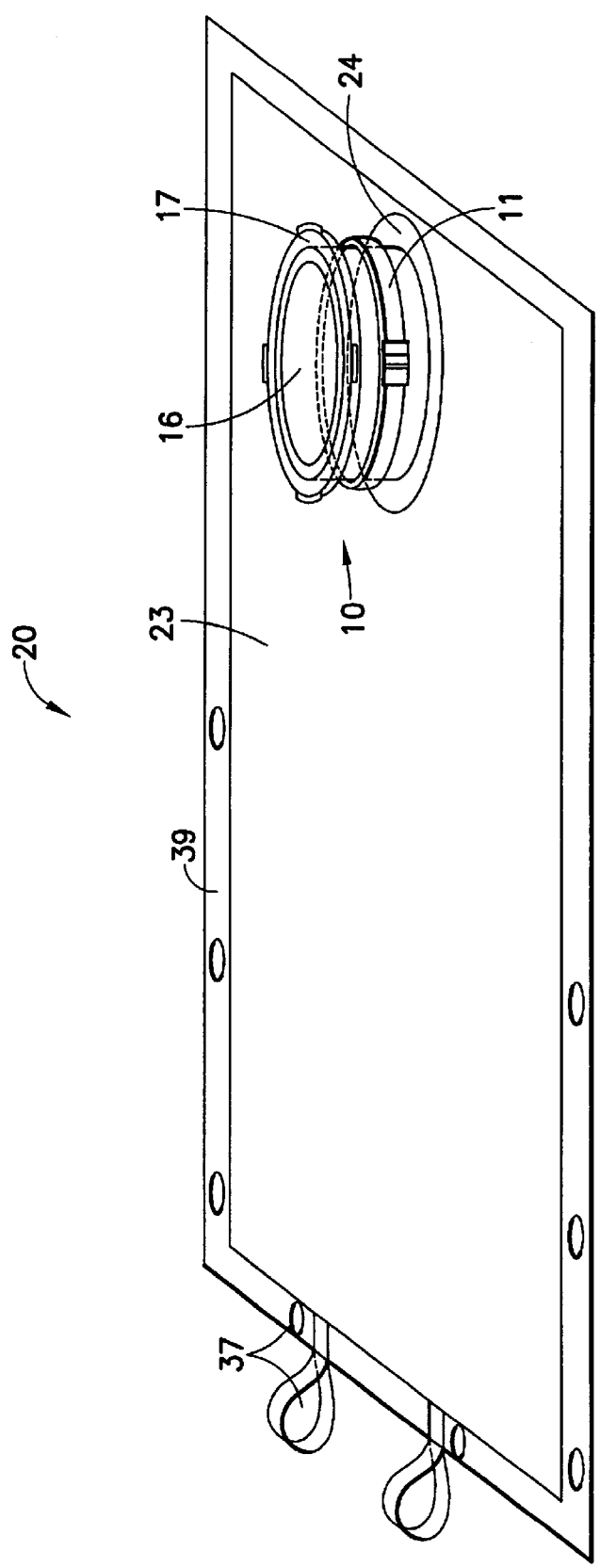
FIG. 2 is a schematic general view of the container combination of FIG. 1.

FIG. 1 is a schematic cross-sectional view through a sterilisable container combination 1 in accordance with a first embodiment of the present invention and a port 32 of a standard isolation system 30. FIG. 2 is a schematic view of the combination 1. The combination 1 comprises three main pieces: a reusable adapter 10, a connector port 22 and a container 20. The adapter 10 is sealably connectable to the connector port 22 and is adapted to fit to the standard port 32 of the isolation system 30. The connector port 22 includes a collar 22A with a flange 24 and an internal bore 26 and the container 20 includes a flexible bag 23 which is sealed to the flange 24. Optionally, the collar 22A may be sealed by a tearable or peelable flap or cover 27. It is preferred if the cover 27 is located at, on or immediately adjacent to the lip of the collar 22A which faces away from the bag 23 (as shown in FIG. 1) but the present invention is not limited thereto. The bag 23 may be open at one end to allow inclusion of sterlized or sterilisable objects or a second inner bag 25 and is preferably closable, e.g. by heat sealing.

Optionally, container 20 may also include a second inner bag 25 which may be optionally and releasably attached to an inside bag holding device 28 on the flap or cover 27. The adapter 10 is in the form of a ring 17 defining an internal bore 12, the ring 17 having a portion 14 for sealable connection to the collar 22A of the container 20. The sealable connection between the collar 22A and the adapter 10 may be completed by a clamp 11 and a seal 13, e.g. a rubber "O" ring. Ring 17 and collar 22A are typically circular in cross-section but the present invention is not limited thereto.

Various materials may be used for making the bag 23 depending upon the application and its requirements. It is preferred if the bag 23 may be made of a single material such as low density polyethylene, high density polyethylene or polypropylene which allows the bag to be recycled, however, it is not always possible to use only a single material. Laminates including inner nylon or aluminum layers may be used and preferably such laminates have an outer thermally sealable layer such as low density or high density polyethylene. The bag 23 may also be made of a breathable material or include breathable sections or patches. A suitable breathable material is Tyvek™ which allows steam to pass through and to sterilize the inside volume 21 and contents of the bag 23. The inner bag 25 having an inner volume 29 may be made of any of the materials described above for the outer bag 23. The inner bag 25 may be open at one end to allow inclusion of sterilized or sterilisable objects and can then be closed by heat sealing. For example, the inner bag 25 may be held by the holding device 28 to the optional flap or cover 27, e.g. heat sealed with a seal (28) or releasably clamped with a mechanical clamp (28). The inner bag may have a long tubular neck (best shown in FIG. 3) which can be drawn through the connector port 20 and be used as a pipe for dispensing the materials from inside inner bag 25. To allow removal of cover or flap 27, a circumferential mechanical weakness 27A may be provided. Cover or flap 27 may be made of a tearable or peelable breathable material such as Tyvek™. Preferably, the cover or flap is removable from the side remote from the bag 23, i.e. access is possible from the isolation system 30.

The bag 23 is preferably sealed to the connector port 22 by heat sealing or any other similar method which provides a high quality hermetic seal. Preferably, the connector port 22 is in the form of a rigid collar 22A with a flange 24. This collar 22A is placed inside the bag 23 and located through a hole therein so that the outer surface of the collar 22A comes in contact with the inner surface of the bag 23. The inner side of the bag material which overlaps the flange 24 is sealed to the outer surface of the flange 24. The collar 22A is preferably made from a material which is heat sealable to the material of bag 23. Suitable materials are, for instance, low density, high density polyethylene or polypropylene. By heat sealing the inside of the bag 23 to the outside of the flange 24 one of the difficulties with the seal of '699 is solved. Whereas the bag to collar seal of '699 tends to peel and open when a load is placed on the bag, the seal of the present invention is much more robust and does not tend to peel when the bag 23 is loaded.

Figure 6:
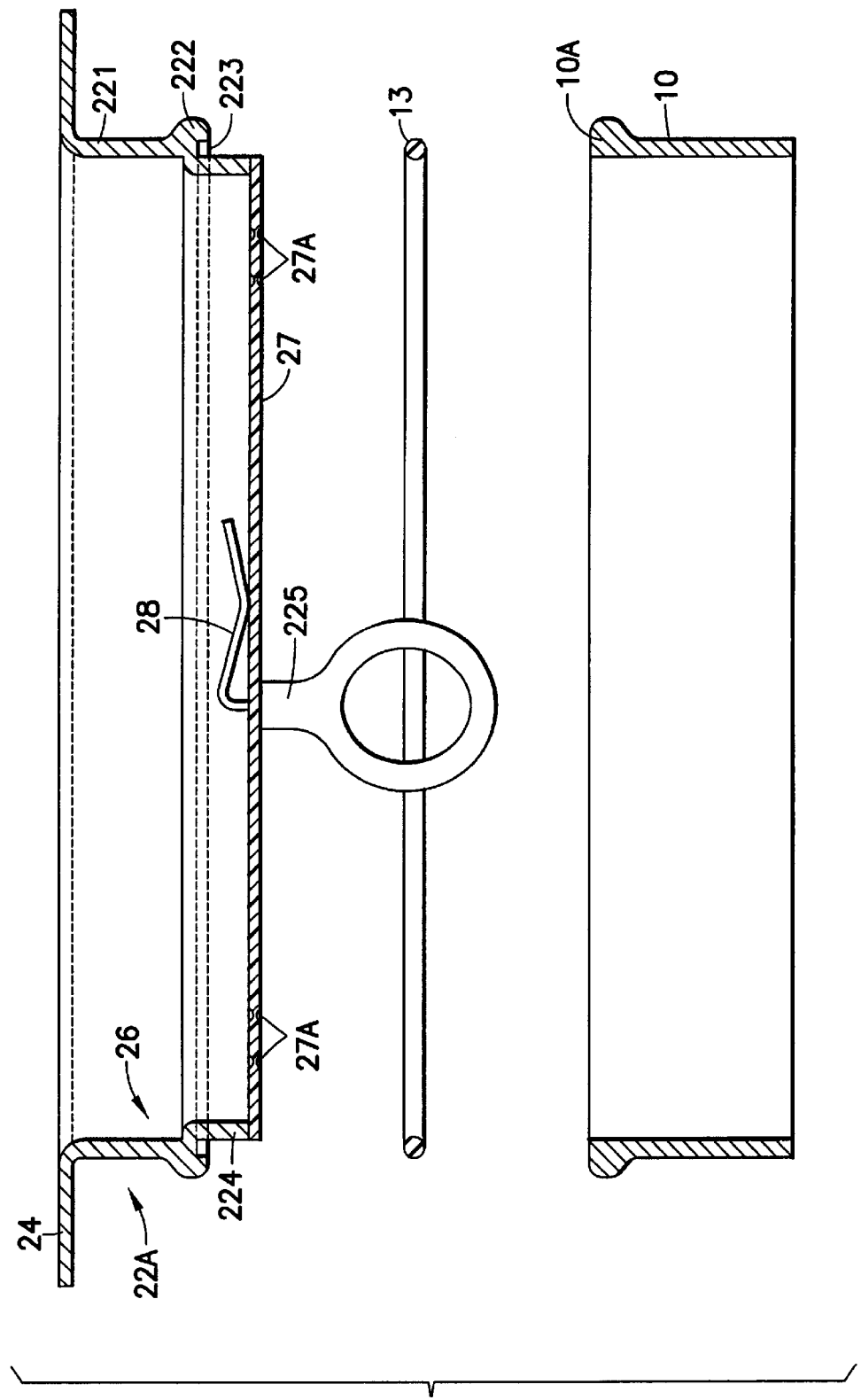
FIG. 6 is a schematic cross-sectional representation of a connector port in accordance with one embodiment of the present invention.

Collar 22A in accordance with an embodiment of the present invention is shown schematically in cross-section in FIG. 6. Collar 22A is generally cylindrical in shape, e.g. circular, square, hexagonal, and includes a first cylindrical portion 221 which is preferably formed integrally with the flange 24. The other end of the first cylindrical portion 221 is terminated by a raised bulbous ring 222 which co-operates with a similar ring 10A on adapter 10 to form a suitable outer mating surface for the clamp 11 when applied. An annular recess 223 is preferably provided in the end surface of the bulbous ring 222 for receipt of a seal 13, e.g. an "O" ring. A second short cylindrical portion 224 is preferably formed integrally with the bulbous ring 222, the first cylindrical portion 21 and the flange 24. The second cylindrical portion 224 has an outer diameter which is smaller than the inner diameter of the recess 223 and the internal diameter of the adapter 10, and is preferably sealed by a tearable or peelable cover film 27 on or adjacent its outer lip. Film 27 may allow passage of sterilizing fluids, e.g. of Tyvek™. Cover 27 may include mechanical weaknesses 27A for assisting in the tearing thereof Further, film 27 may be provided with a pull-ring 225 which eases tearing or pealing film 27. Film 27 may include an inner bag holding device 28 on its inside (shown here as a clip).

As shown best in FIG. 2, the edges of bag 23 are preferably provided with reinforcing 39 and with attachment or lifting holes and/or tabs 37 to improve handling. Sealingly connected to the connector port 22 is an adapter 10. This adapter 10 is designed so that its end 17 remote from the connector port 22 fits into a standard port 32 of an isolation system 30. Hence, adapter 10 adapts the connector port 22 to the dimensions of the standard inlet port 32 of the isolation system 30. Preferably, the adapter 10 is reusable. The combination of the bag 23 and the connector port 22 may be reusable but it is normally more economic to recycle the material rather than reuse the combination 22, 23. Important advantages of the adapter 10 and the collar 22A are that the inner bore of the adapter 10 is sterilisable before the adapter 10 is docked to the inlet port 32 of the isolation system 30 and that standard bags 23 and connector ports 22 can be produced and the necessary re-usable adapters 10 fabricated to adapt the standard collars 22 to the inlet opening 32. This reduces inventory and unit cost. Adapter 10 may be made from any suitable material which meets the requirements of the particular application. Typically the adapter 10 will be made of metal or more preferably a plastic material such as polypropylene, high density polyethylene, PTFE, polycarbonate or Lexan™. An end portion 14 of the adapter 10 remote from the portion 17 is configured to provide a sealing connection to the connector port 22. For example, the adjacent end surfaces of the connector port 22 and the end portion 14 of the adapter 10 may be configured to provide an "O" ring seal using a rubber "O" ring 13 and a metal clamp 11. The metal clamp 11 is applied to standardized dimensions on the outside of the collar 22A and the adapter end 14, therefore the clamping effect is reliable and repeatable.

The adapter 10 is configured to fit the standard inlet opening 32 of the isolation system 30. As one possible configuration, the end opening 12 of the adapter 10 is preferably sealed by a door 16 which may be sealed to the inner bore of adapter 10. On the end surface of the door 16 an aggressive pressure sensitive adhesive 18 may be applied and protected by a release paper (not shown), In the inlet port 32 of the isolation system 30 there may be a corresponding door 34 located in a housing 36 and provided with a hermetic seal 35 between the door 34 and the housing 36 The housing 36 is located in the wall 38 of the isolation system 30. The housing 36 has internal dimensions which allow receipt of the adapter 10.

Figure 4D:
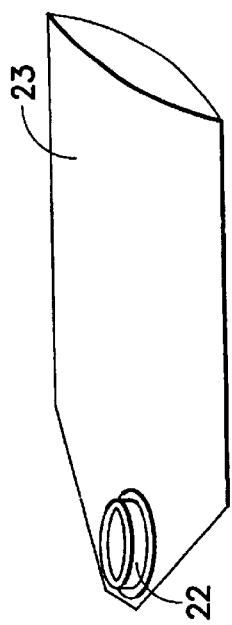
FIG. 4 is a schematic representation of various designs of container combinations in accordance with the first embodiment.
Figure 4E:
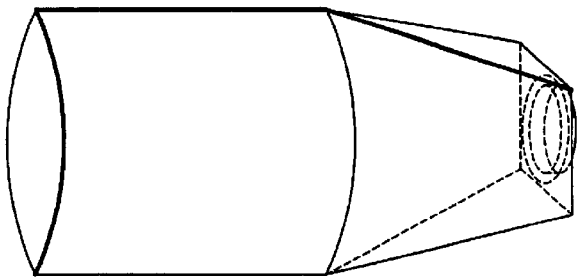
Figure 4A:
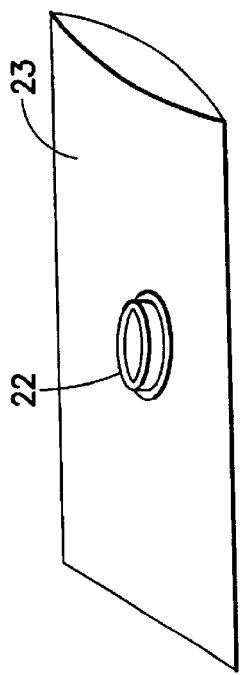
Figure 4B:
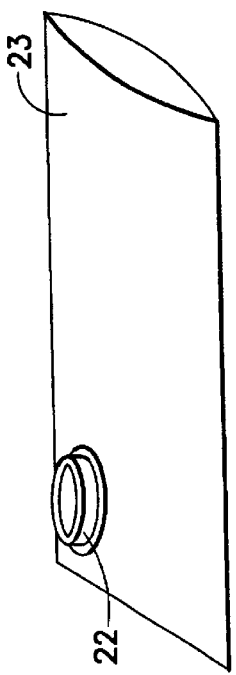
Figure 4C:
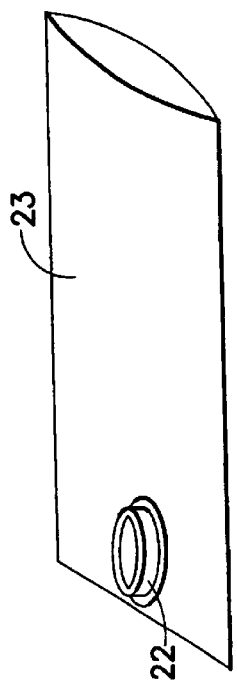

Alternative shapes of container 20 are shown schematically in FIGS. 4A to 4E. FIGS. 4A to D show lay flat flexible bags 23 with the connecting ports 22 arranged in various positions. FIG. 4E shows a modified flexible bag 23 including a front face perpendicular to the main lay-flat bag 23 in which the connecting port 22 is sealed. A method of manufacturing this container 20 will now be described.

Figure 8:
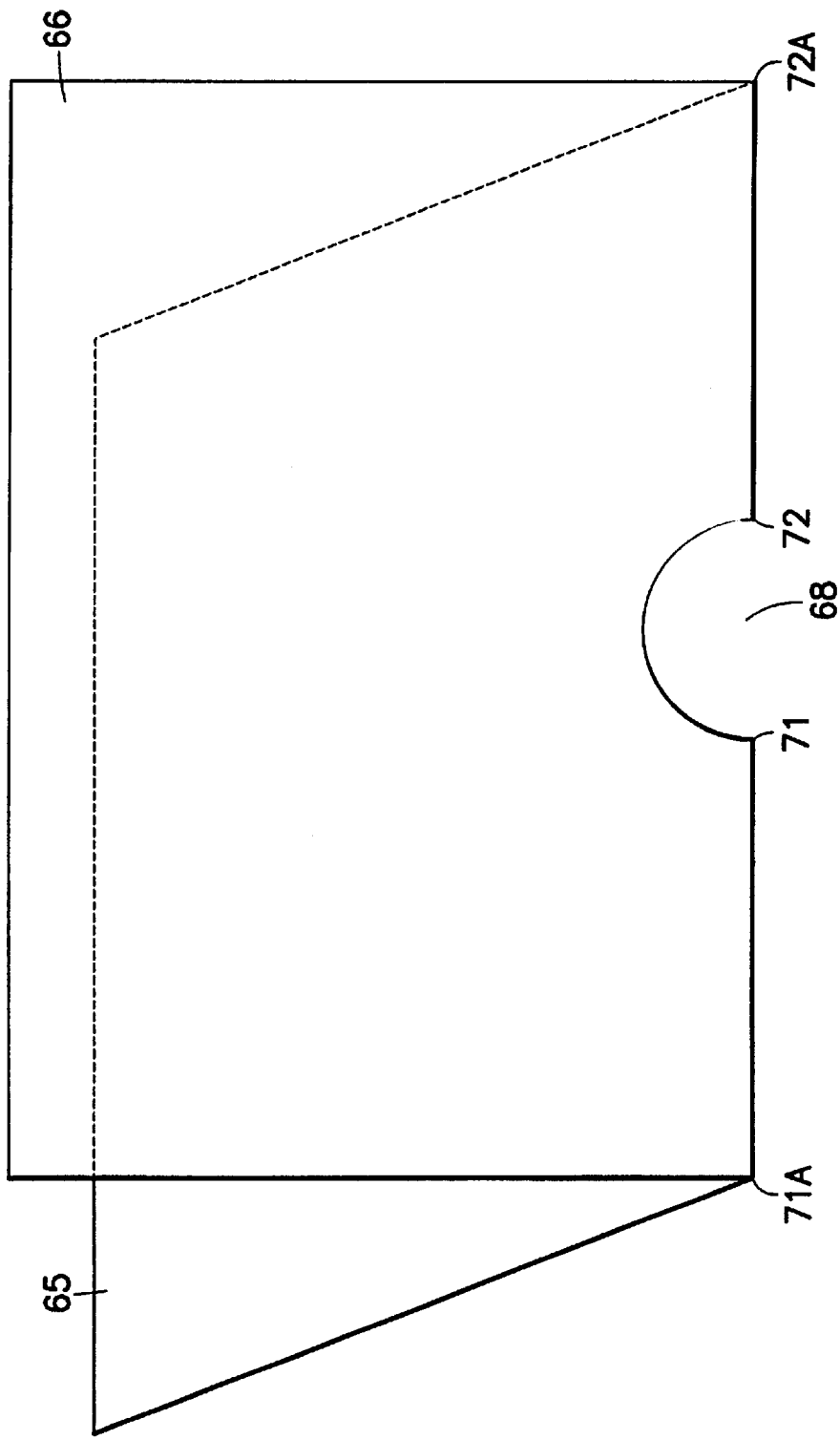
FIGS. 8 to 11 show steps in the formation of a flexible sheet enclosure with a port perpendicular to the plane of the sheet material of the type shown schematically in FIG. 4E.
Figure 9:
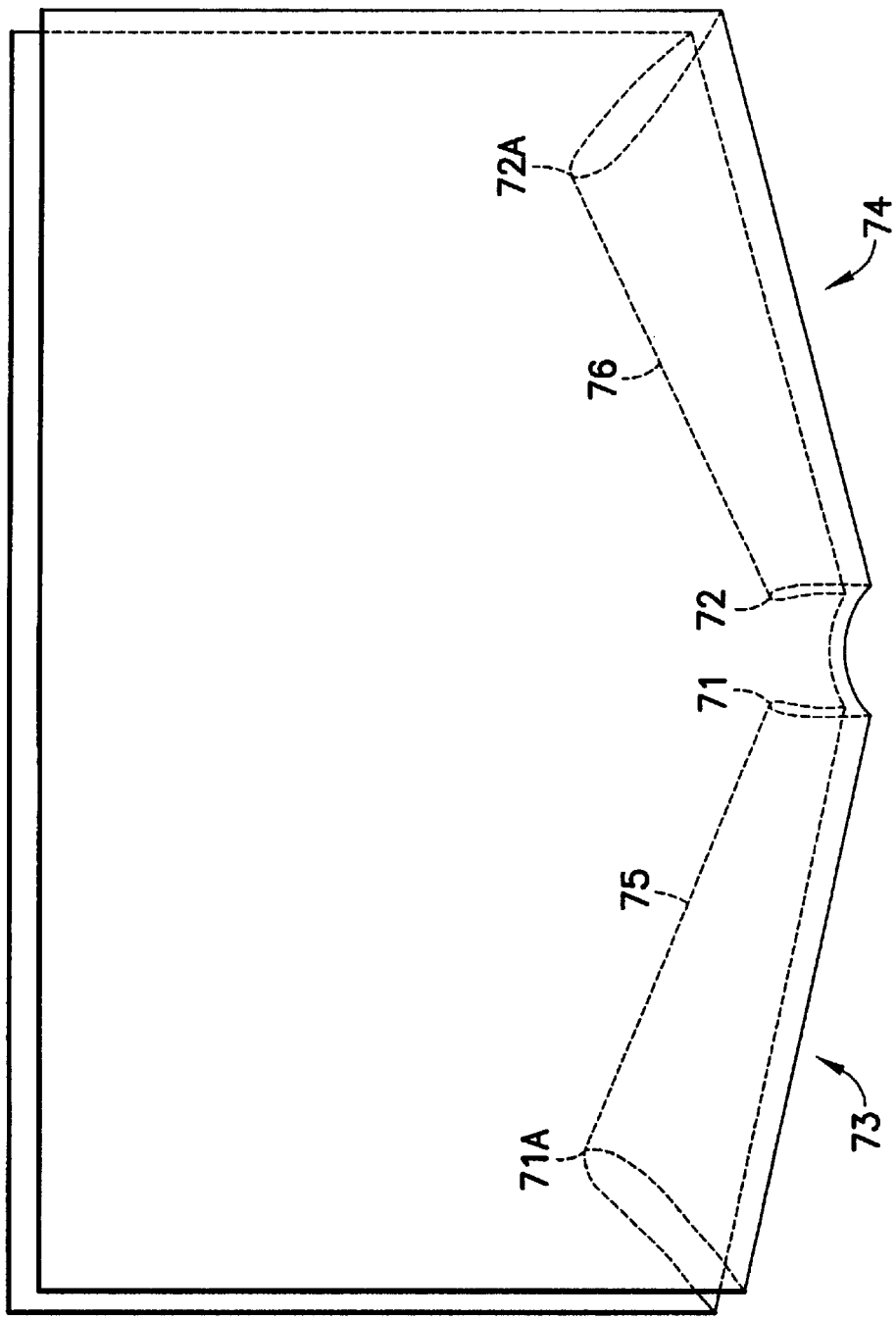
Figure 10:
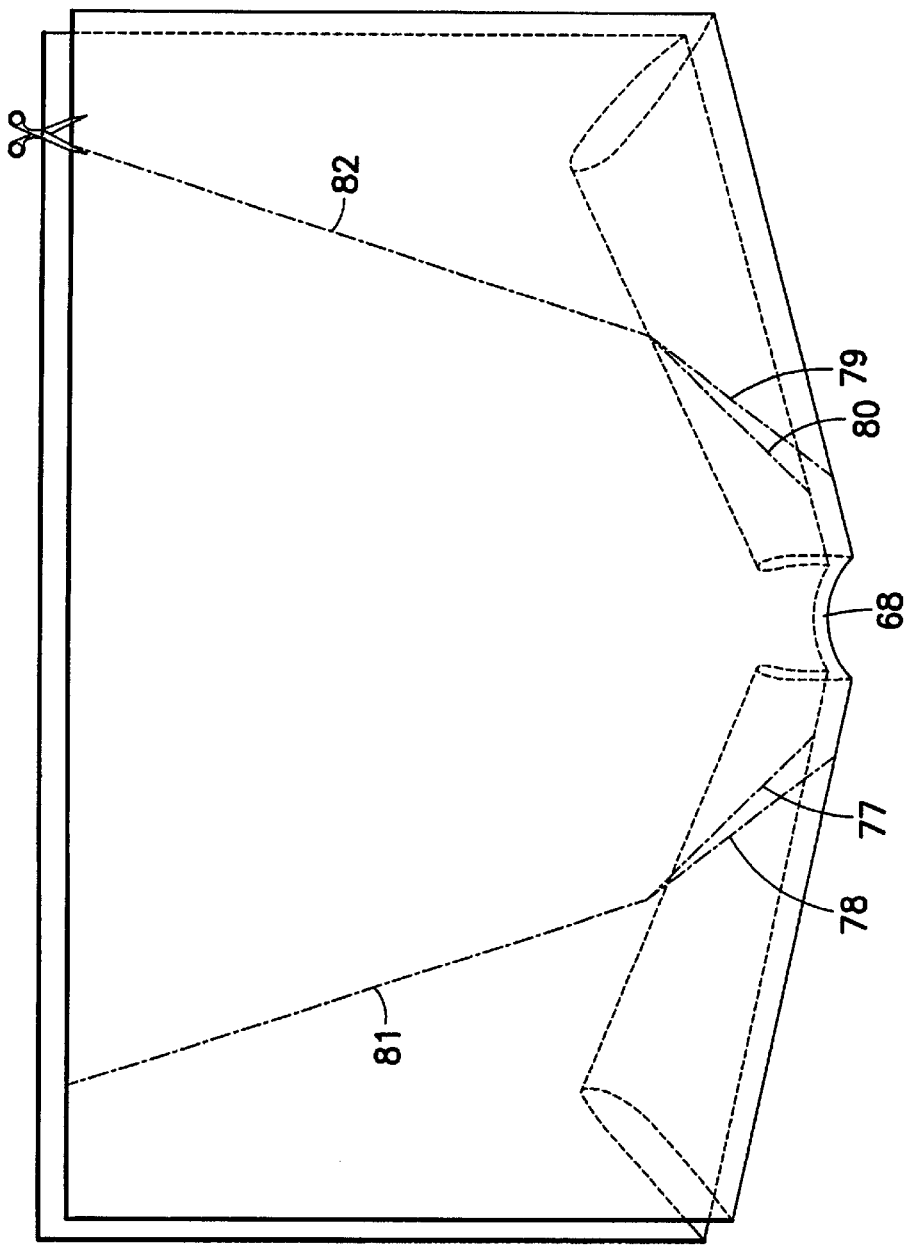
Figure 11:
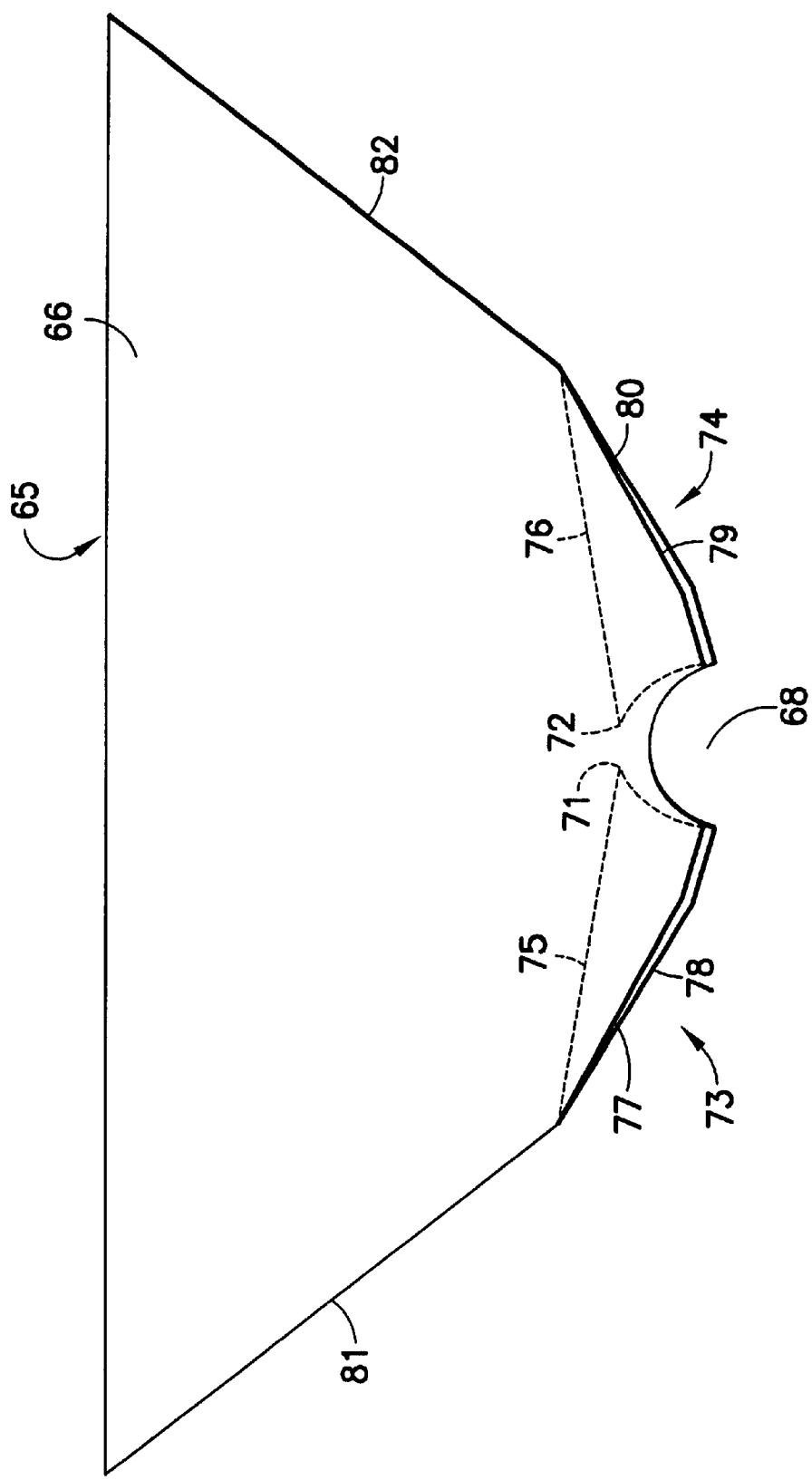
Figure 12:
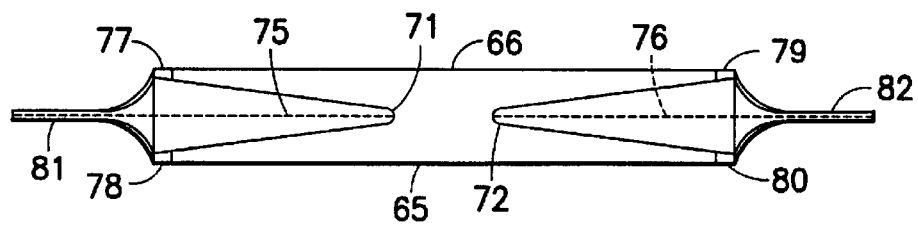
FIG. 12 is a schematic cross-section through a part of the flexible sheet container shown in FIG. 11.
Figure 13:
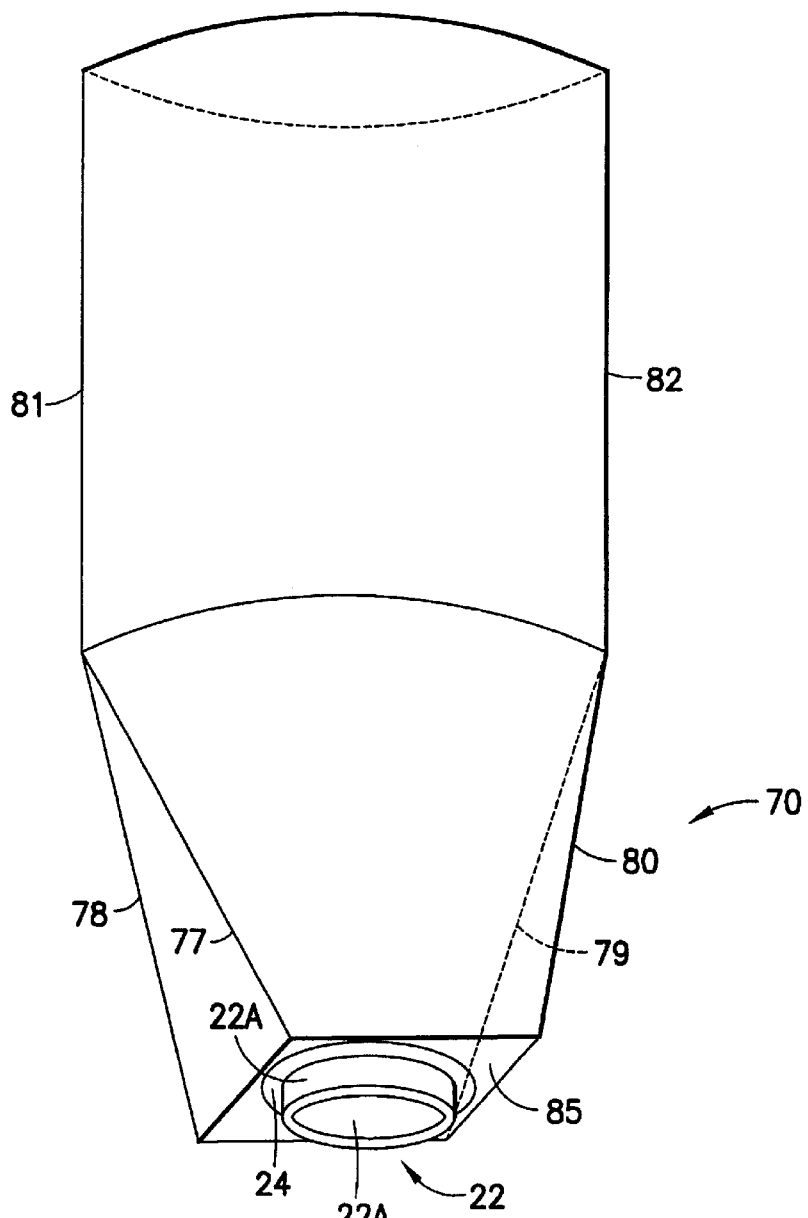
FIG. 13 is a schematic view of the completed sheet enclosure described with reference to FIGS. 8 to 12.

As shown in FIG. 8 a flat piece of sealable flexible material is folded in two to form two sheets 65, 66 on top of each other and a fold 67. A half-circular opening 68 is cut out of a portion of the fold 67 of the material. Reference numbers 71, 72 represent the fold ends where the half-circle 68 cuts the fold 67. Reference numbers 71A, 72A represent the extreme fold ends on the outer edge of the sheet material. As shown in FIG. 9 the folds 67, 68 are formed into tucks 73, 74 by tucking ends 71 and 71A and 72 and 72A into the space between the two sheets 65, 66 to form one tuck 73, 74 on each side of the opening 68 respectively. Each tuck 73, 74 has an upper fold 75, 76, respectively which is a part of the folds 67, 68, respectively but with the fold in the opposite direction. First seals 77, 78 and 79, 80 are formed on each of the tucks as best shown in FIG. 10 by placing a heat-resistant material inside the tucks 73, 74 or by treating the inside mutually opposing surfaces of each tuck 73, 74 to make these surfaces non-sealable. A V-shaped sealing structure is formed in the sheets 65, 66 as shown in FIG. 10. The first seals 77–80 may be thermal welds or heat seals. A section through the fold ends 71, 72 is shown in FIG. 12. As can be seen, four seals 77–80 are formed with the folds 75, 76 lying between. In addition second seals 81, 82 are formed between sheet materials 65, 66. By trimming away excess sheet material from the seals 77–82 a flexible sheet container 70 is formed as shown in FIG. 11. This container 70 may be opened-out in the form of a truncated cone-shaped structure with an opening 68 at its smallest end. Following an edge of the sheets 65, 66 there is a seal 8i between the two sheets 65, 66. This seal 81 merges into two seals 77, 78 which define the tuck 73. Seals 77, 78 merge into folds 83, 84 which terminate at the opening 68. The other edge of the flexible sheet container 70 is similar. A connector port 22, preferably of circular cross-section, with a collar 22A having a flange 24 and an internal bore 26 is now pushed into the opening 68 from the within the cone-shaped structure as shown in FIG. 13. Due to the construction of the cone-shaped structure as explained above a flat portion 85 of sheet material lies snugly against the outer surface of the flange 24 so that an inner surface of the flat portion of the sheet material is in contact with the outer surface of the flange 24. This flat portion 85 does not contain any welds or seals or double thicknesses of sheet material. Hence, this flat portion 85 may be easily sealed to the flange 24, e.g. by heat sealing. The connector port 22 may be provided with a portion for sealable connection to an adapter 10 using a seal such as an "O" ring 13 and a clamp 11 as has been described above. The port 22 may include a cover 27 as described with reference to any of the embodiments of the present invention. In particular the cover 27 may include an inside bag holding device 28 as described with reference to any of the embodiments of the present invention. An inside bag 25 may be installed from the open end of container 70 and secured to holding device 28. The device. of FIG. 13 is particularly suited for the transfer of bully items which cannot pass a 90° bend as present in the containers shown in FIGS. 4A to D, for example.

FIG. 14 shows how the device of FIG. 13 may be assembled into a temporary isolation room 90. Two devices as shown in FIG. 13 are sealed together at the openings remote from connector port 22. Glove ports 92, 94 may be provided in the temporary isolation room 90. Each of the connector ports 22 is now fixed to the communication port of another device, e.g. another container or to the communication port of a fixed isolation area using an adapter 10 as described above. Items may now be transferred from a container into the temporary isolation room 90. Here they may be manipulated through the glove ports 92, 94. The items may now be returned to the container from which they came, transferred to another container or transferred to an isolation area depending on what is connected to the connector ports 22 of the temporary isolation room 90.

Figure 5A:
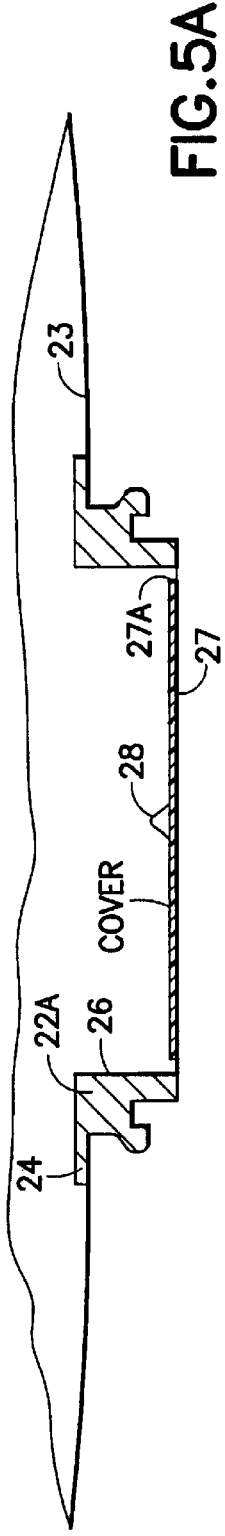
FIG. 5 is a cross-sectional schematic representation of a container combination in accordance with a second embodiment of the present invention.
Figure 5B:
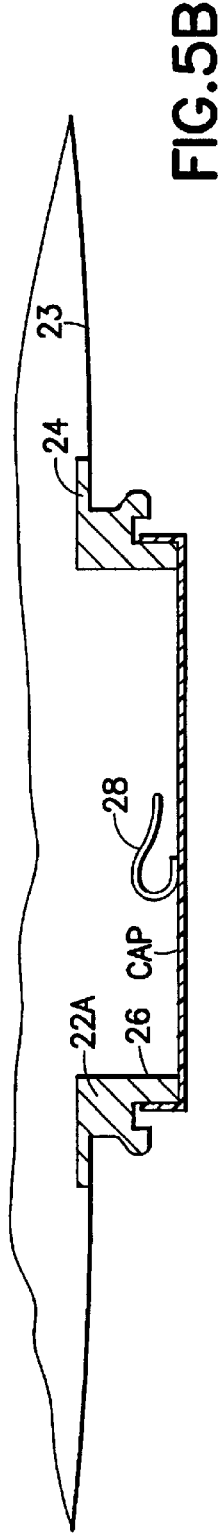

FIGS. 5A to D show various schematic ways of forming the cover 27 on the outer opening of the connecting port 22 any of which may he used with any of the embodiments of the present invention. In FIG. 5A cover 27 is provided with an annular mechanical weakness 27A as has already been described with to respect to FIG. 1. Cover 27 may optionally be provided with an inner bag mechanical holding device 28 or a plug 28 of material for welding and for holding an inner bag 25. FIG. 5B shows an alternative embodiment of the cover 27 in the form of a cap. This cap 27 may be used as an alternative to cover 27 of FIG. 5A or in addition thereto, especially as a mechanical protection for the cover 27 of FIG. 5A Cap 27 extends over and seals off the outer opening of the collar 22A. The inner diameter of cap 27 may be an interference fit with the outer diameter of collar 22A or may be heat sealed to the end thereof. When cap 27 is used without an inner cover 27 as shown in FIG. 5A it may include an inner bag fixing means 28 on its inside, e.g. a clip.

Figure 5C:
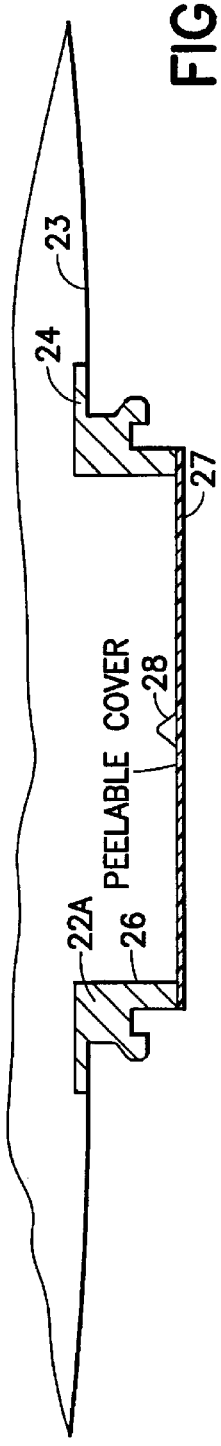
Figure 5D:
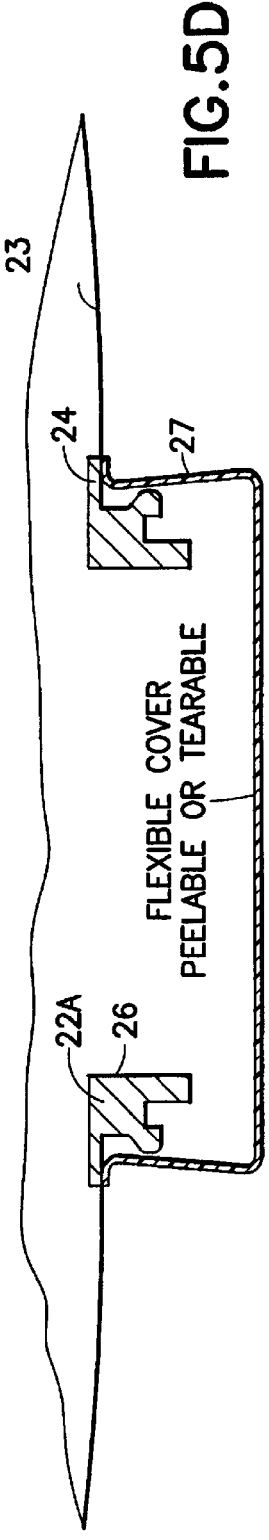

FIG. 5C shows a further embodiment of the cover 27 which may be used as an alternative to cover 27 of FIG. 5A and may be used with or without the cover 27 of FIG. 5B. A peelable cover 27 is peelably and sealably fixed to the outer surface of the collar 22A. Peelable cover 27 may include any of the inner bag fixing devices 28 mentioned for the previous embodiments, FIG. 5D shows a further flexible cover 27 which is an alternative to any of the covers 27 shown in FIGS. 5A to D or may be used in addition thereto. Flexible cover 27 extends over the outer opening of the collar 22A so that it not only can seal off this opening but also protects the sealing surfaces of collar 22A from contamination during transport. The inner diameter of the flexible cover 27 may be an interference fit with the outer diameter of collar 22A or may be peelably or tearably sealed to the outside of bag 23 on flange 24. Flexible cover 27 may include on its inner side any of the inner bag fixing means 28 described with respect to the previous embodiments as shown in any of FIGS. 5A to C.

The container combination 1 of the present invention may be used in several different ways. Firstly, the connector port 22 are installed in the bag 23 and the collar 22A is inserted through the hole in bag 23. The inner side of the bag 23 overlapping the flange 24 is heat sealed thereto. One or more of the covers 27 of FIGS. 5A to D may then be attached to collar 22A. Alternatively, the cover 27 may be attached to the collar 22A before the flange 24 is sealed to the inside of the bag 23. The inner bag 25 may introduced into bag 23 and be fixed to one of the covers 27 using one of the inner bag holding devices 28 described with respect to FIGS. 5A to D and then filled with items to be sterilized and sealed. The outer bag 23 may be sealed at the same time. The adapter 10 is then sealably fixed to the connector port 22 using seal 13 and clamp 11. The complete container combination 1 now appears as in FIG. 2. The container combination 1 is then sterilized by gamma radiation, ethylene oxide or steam as appropriate. Where steam or gas is used, it is preferred if suitable patches of breathable material are provided such as Tyvek™ to allow penetration of the sterilg fluid. In particular, it is preferred if cover or flap 27 is made from a breathable material such as Tyvek™ and/or similar patches are provided on bag 23. In this case the inner bore of the connector port 22 as well as the back surface of door 16 is sterilized Alternatively, cover or flap 27 may be omitted leaving a simple opening 26. Once the complete container combination 1 is sterilized it may be checked by quality control and shipped to the isolation system 30. As is known to the skilled person standard inlet ports 32 usually have quick fastening and locking system to provide a secure hermetic seal. Such an inlet port is supplied by la Calhene, Velizy, France. The adapter 10 is attached to the port 32 and the contaminated sides of doors 16 and 34 fixed together (eg. by the pressure sensitive adhesive on door 16) to trap any contamination. The combination of doors 16 and 34 is now broken away and removed to the inside of the isolation system 30. Now the cover or flap 27 (if present) is removed towards the isolation system 30 pulling the inner bag 25 with it. The inner bag 25 is then pulled at least partly into the isolation system 30 and its contents removed and a new door 34 sealed to the housing 36. Now the empty container combination 1 may be removed and the bag 23 and collar 22A separated from the adapter 10 by releasing the clamp 11.

An alternative way of using the present invention is to supply the container 20 having the connecting port 22 already attached and sealed by one or more of the covers 27 described with reference to FIGS. 5A to D. The bag 23 is open along one side. The bag 23 is filled through this opening and this opening is then sealed, e.g. by heat sealing. A cover 27 in accordance with FIG. 5E is applied to keep the sealing surface of the collar 22A free of contamination. Now the container 20 and its contents can be sterilized by any suitable method. The filled container 20 is then shipped to the location of the isolation port 32. In a suitable clean room the outer cover 27 may be removed and the collar 22A attached to a sterilized adapter 10 and sealed and clamped with the seal 13 and clamp 11. Now the complete combination 1 can leave the clean room if required before being docked to an isolation port 32 and the contents of bag 23 transferred through the adapter 10 and the connector port 22.

In the above only two methods of using the present invention have been described. However, the present invention as described has such flexibility that many ways may be devised for transferring sterilized materials using the components described above, all of which are included as embodiments of the present invention.

While the invention has been shown and described with reference to preferred embodiments, it will be understood by those skilled in the art that various changes or modifications in form and detail may be made without departing from the scope and spirit of this invention as defined in the claims.

Figure 3:
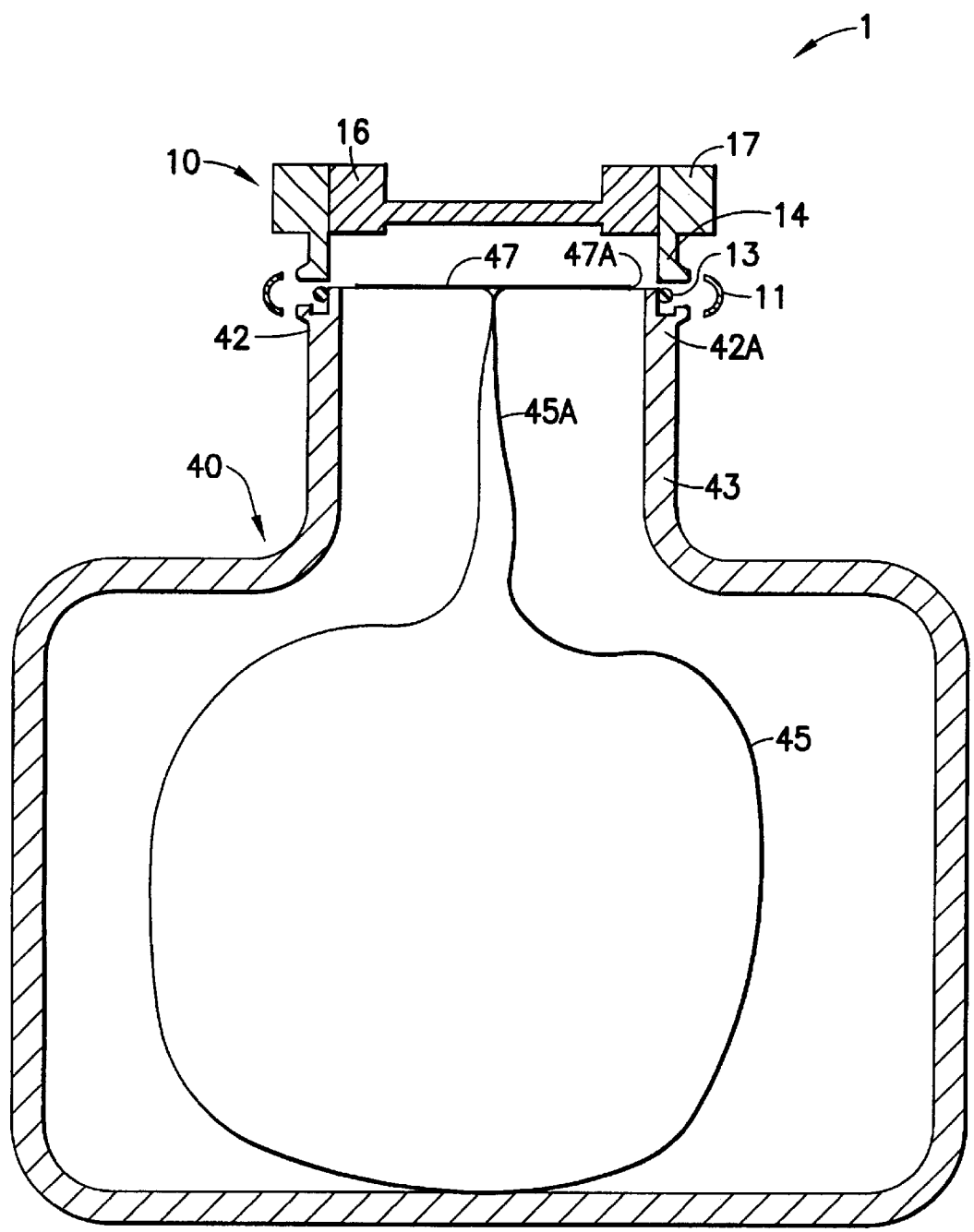
FIG. 3 is a cross-sectional view of an embodiment of the container combination of FIG. 1.

For example, the present invention has been described with reference to flexible bags 23, 25, however, the invention is not limited thereto. As an example, FIG. 3 shows a cross-sectional schematic representation of a second embodiment of the container combination 1 of the present invention. It includes a rigid blow-molded canister 43 which has a connector port 42 formed on one end. Connector port 42 has an integral shaped collar section 42A which co-operates with an "O" ring seal 13 and a clamp 11 to form a sealed connection to an adapter 10. The canister 43 may contain an inner flexible bag 45 attached to a flap or cover 47 by means of an inner bag holding device 28 as described with respect to the first embodiment. Inner flexible bag 45 may have a long narrow neck portion 45A which may be drawn through the connector port 42 and used as a discharge tube for items in the inner bag 45. Cover 47 may be similar in form and function to any of the covers 27 described with reference to FIGS. 5A to D. Cover 47 may be, for example, peelable or include a mechanical weakness 47A which allows removal of a central portion of the flap or cover 47 by tearing. The canister 43 when sealably connected to the adapter 10 by means of a seal 13 and clamp 11 forms a container combination 1 in accordance with the present invention and may be used as generally described for the first embodiment.

Further, the present invention includes manufacturing a plurality of similar or different bags 23 or canisters 43 and providing each with a connector ports 22, 42 respectively having a standard connecting structure and dimensions to fit to adapters 10. Further a plurality of adapters 10 may be provided, each adapter 10 having on one end the structure and dimensions necessary to fit to one of the inlet openings 32 of a commercially available isolation system 30. The other end of the adapter 10 has a standard structure and dimensions to form a hermetic sealing connection with the connector ports 22, 42 of a container combination 1 according to the present invention.

Figure 7:
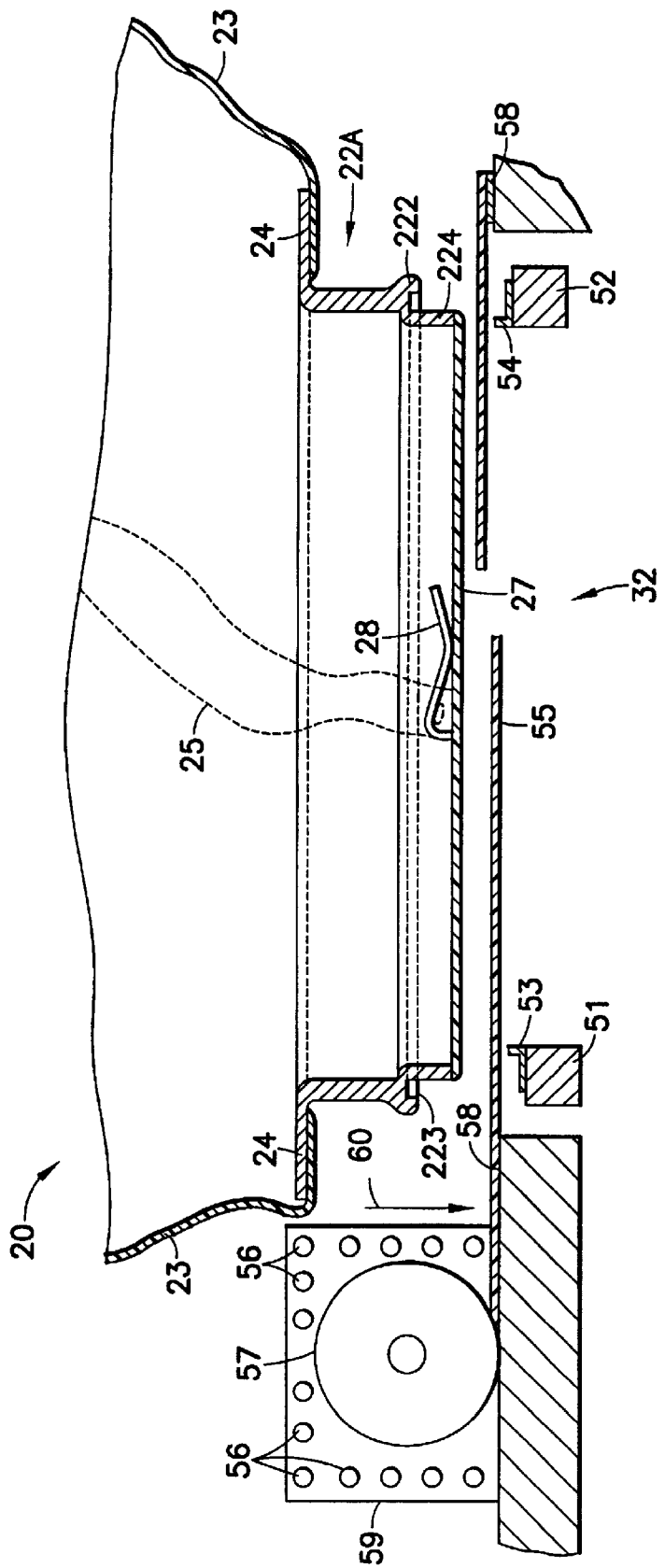
FIG. 7 shows use of a connector port according to another embodiment.

In addition, the present invention is not limited to use of an adapter 10. A further embodiment of the present invention is shown schematically in cross-section in FIG. 7. The collar 22A and its attachment to the outer bag 23 is generally as described with respect to the previous embodiments (or may be a collar 42A of a container 40) and in particular is similar to that shown in and described with reference to FIG. 6 except without the pulling 225. The outer lip of the second cylindrical portion 224 of the collar 22A is sealed with a breathable or a non-porous film or cover 27. An isolation port 32 of an isolation system 30 is initially sealed by a sterilized film 55 which is drawn from a roll 57 of such material in a sterile box 59. Sterile box 59 may be kept sterile by various means including heaters 56. The film 55 is removably sealed to the outer rim of the port 32 by means of seals 58 and releasable clamps (not shown for clarity purposes). Both the collar 22A and the isolation port 32 are preferably rectangular in cross-section, but the present invention is not limited thereto. Preferably, the container 20, 40 is delivered to the isolation port 32 with the insides of bag(s) 23 and 25 (if present) sterilized as has been described above. Inner bag 25 (if present) is preferably attached to the inner bag holding device 28, e.g. by a clip. The film cover 27 and the collar 22A may be protected by a cap as shown in, and described with respect to FIG. 5D. Just before docking to port 32, this outer cap is removed and collar 22A is sealingly clamped in close proximity to the sterilized film 55 by clamps (not shown for clarity reasons) which locate and seal onto the bulbous ring 222 and/or the outer diameter of the second cylindrical portion 224 of the collar 22A and/or onto an "O" ring in the annular recess 223. One way of doing this is to form the adapter 10 of FIG. 1 (without the door 16) integrally with isolation system 30 so that once the clamp 11 has been applied, the container 20, 40 is sealed and clamped to the isolation system 30. Moveable heat sealers 51 and 52 including hot knives 53, 54 respectively, are now brought against the side of the film 55 towards the isolation zone 30 and the outer edge of a central portion of cover film 27 is heat sealed to the film 55 thus trapping any contamination therebetween as well as optionally, heat sealing the film 55 to the end surface of the second cylindrical portion 224. Also the knives 53, 54 cut through (e.g. melt through) the films 55 and 27 thus opening the container 20. The combined films 27, 55 are now drawn into the isolation system 30 pulling with them the long narrow tubular neck (shown best in FIG. 3, 45A) of the inner bag 25 if present. The contents of bag 23 and/or inner bag 25 may now be removed. The clamps on seals 58 are released and film 55 is cut thorough by knife 60. The piece of film 55 attached to the outer ring of second cylindrical portion 224, bag 25 (if present) and the cut and sealed pieces of film 27, 55 are now pushed back into the container 1. The opening 32 is now resealed by drawing a further piece of film 55 across the opening 32 from roll 57 and sealing the film 55 thereto by clamping onto the seals 58, Now the sealing clamps on the ring 222 may be released and the container 1 discarded.

The container combinations 1 of the present invention provide the advantage that standard bags and canisters 23, 43 and standard connector ports 22, 42 may be used and, by use of a reusable adapter 10, these may be adapted to the various types of inlet ports of isolation systems which are available on the market or may yet be developed One aspect of the present invention is to provide a standard sealing and connection interface between the adapters 10 and the connector ports 22, 42. The present invention also allows the double security of an inner and outer bag or canister. A simple reliable means of sealing the flexible outer bag to the flange of the collar 22A is also provided. Further, by making the cover or flap 27, 47 breathable, the inner surface of the adapter can be sterlized before the container combination 1 is shipped thus avoiding an additional sterilizing step after the adapter 10 has been fixed to the inlet port of the isolation system. By attaching an inner bag 25, 45 to the flap or cover 27, 47 which is removable in the direction of the isolation system 30, the inner bag 25, 45 may be easily emptied into the isolation system 30 while still being in a sealed state. This provides not only ease of handling but also improved cleanliness.

What is claimed is:

1. A sterilisable container combination comprising;
   an outer container having an opening;
   a hollow connector port having an internal bore, wherein an inner surface of the outer container being sealingly secured to an outer surface of the hollow connector port so that the opening in the outer container is in registry with the bore of the hollow connector, wherein said internal bore has a first opening in communication with an external environment and a second opening in communication with said outer container's interior;
   a removeable cover, wherein said removable cover is removabley sealed to said first opening isolating said internal bore from, said external environment; and
   an adapter having an internal bore, the hollow connector port and the adapter being sealably connectable by a clamping and sealing device so that the internal bores of the hollow connector port and the adapter are in open communication.

2. A sterilisable container combination according to claim 1, wherein the adapter has a removable door sealed to the end of the adapter remote from the sealable connection to the hollow connector port.

3. The sterilisable container combination according to claim 1 wherein the outer container is a flexible bag.

4. A sterilisable container combination according to claim 3, wherein the flexible bag has a hole in a flat portion thereof and the hollow connector port includes a collar portion and a flange and an inside surface of the flexible bag is sealed to an outside surface of the flange.

5. The sterilisable container combination according to claim 1, wherein the hollow connector port has a removal cover.

6. The sterilisable container combination according to claim 5, wherein the removable cover includes an inner bag holding device.

7. The sterilisable container combination according to claim 1, further comprising an inner flexible bag within the container.

8. The sterilisable container combination according to claim 7, wherein the hollow connector port has a removal cover and the inner bag is attached to the removal cover.

9. A sterilisable container device comprising:
   an outer container and an inner flexible container, the outer container including a hollow connector port, wherein said hollow connector port has a first opening in communication with an external environment and a second opening in communication with said inner flexible container's interior, and wherein the hollow connector port being sealed by a removable cover, wherein said removable cover is removabley sealed to said first opening isolating internal surfaces of said hollow connector port and said inner flexible container from said external environment; and the removable cover including a holding device on the side of the cover towards the inner flexible container for holding the inner flexible container.

10. The sterilisable container device according to claim 9, wherein the outer container is a flexible bag.

11. The sterilisable container device according to claim 10, wherein the flexible bag has a hole in a flat portion thereof and the hollow connector port includes a collar portion and a flange and an inside surface of the flexible bag is sealed to an outside surface of the flange.

12. A sterilisable container device comprising:

a flexible bag, the bag having a hole in a flat portion thereof and a hollow connector port fixed thereto, wherein said hollow connector port has a first opening in communication with an external environment and a second opening in communication with said flexible bag's interior, and wherein the hollow connector port being seared by a removable cover, wherein said removable cover is removabley sealed to said first opening isolating internal surfaces of said hollow connector port and said inner flexible container from said external environment, and wherein the hollow connector port including a collar portion and a flange, and an inside surface of the flexible bag being sealed to an outside surface of the flange.

13. The sterilisable container device according to claim 12, wherein the hollow connector sort has a removal cover.

14. The sterilisable container device according to claim 13, wherein the removable cover includes an inner bag holding device.

15. The sterilisable container device according to claim 12, further comprising an inner flexible bag with the container.

16. The sterilisable container device according to claim 15, wherein the hollow connector port has a removal cover the inner bag is attached to the removable cover.

17. A plurality of sterilisable container devices, each having an opening and a hollow connector port having an internal bore, wherein said hollow connector port has a first opening in communication with an external environment and a second opening in communication with said sterilisable container devices's interior, and wherein the hollow connector port being sealed by a removable cover, wherein said removable cover is removabley sealed to said first opening isolating internal surfaces of said hollow connector port and said sterilisable container devices from said external environment, and wherein each container device being sealingly secured to the hollow connector port so that the opening in the container is in registry with the bore of the hollow connector port; and a plurality of different adapters suitable for connecting to the inlet ports of different isolation systems, each adapter having an internal bore, the hollow connector ports and the adapters being sealingly connectable by a common size of connecting and sealing devices so that the internal bores of the hollow connector port and the adapter are in open communication.

18. A method of connecting a sterilized container to the inlet port of an isolation system, comprising the steps of:

providing a container device with a connection port securely sealed to the container device, wherein said connection port has a first opening in communication with an external environment and a second opening in communication with said sterilized container's interior, and wherein said connection port being sealed by a removable cover, wherein said removable cover is removabley sealed to said first opening isolating internal surfaces of said connection port and said sterilized container from said external environment;

sealingly connecting a first end of an adapter to the hollow connector port of the container device; and docking and sealing a second end of the adapter to the inlet port of the isolation system.

19. A method of producing a sterilisable container, comprising the steps of:

providing a flexible sheet enclosure with a flat portion;

providing a hole in the flat portion of the flexible sheet enclosure and fixing a hollow connector port thereto, the hollow connector port including a collar portion and a flange portion defining an internal bore of the hollow connector port, wherein said hollow connector port has a first opening in communication with an external environment and a second opening in communication with said flexible sheet enclosure's interior, and wherein said connection port being sealed by a removable cover, wherein said removable cover is removabley sealed to said first opening isolating internal surfaces of said connection port and said flexible sheet enclosure from said external environment; and sealing the inside surface of the flexible sheet enclosure to an outside surface of the flange portion, she collar portion extending through the hole in the flexible sheet enclosure.

20. The method according to claim 19, wherein the enclosure extends in one direction to form the container and the sheet material forms the walls of the container the flat portion is provided by a front face of the sheet enclosure perpendicular to the extension direction of the container and the hole is provided to in the front face.

* * * * *